(12) United States Patent
Taormina

(10) Patent No.: US 8,398,396 B2
(45) Date of Patent: Mar. 19, 2013

(54) SURGICAL DRILL TEMPLATES AND METHODS OF MANUFACTURING THE SAME

(75) Inventor: Matteo Taormina, Zürich (CH)

(73) Assignee: Straumann Holding AG, Basel (CH)

( * ) Notice: Subject to any disclaimer, the term of this patent is extended or adjusted under 35 U.S.C. 154(b) by 191 days.

(21) Appl. No.: 12/752,459

(22) Filed: Apr. 1, 2010

(65) Prior Publication Data

US 2010/0255441 A1 Oct. 7, 2010

(30) Foreign Application Priority Data

Apr. 2, 2009 (EP) .................................. 09157189

(51) Int. Cl.
*A61C 3/00* (2006.01)
(52) U.S. Cl. ........................................................ 433/75
(58) Field of Classification Search .................. 433/72, 433/75–76, 172–176, 214, 215; 434/263, 434/270; 623/11.11, 901; 700/117–120
See application file for complete search history.

(56) References Cited

U.S. PATENT DOCUMENTS

| | | | | |
|---|---|---|---|---|
| 5,320,529 A * | 6/1994 | Pompa | .......................... | 433/76 |
| 5,718,579 A * | 2/1998 | Kennedy | ........................ | 433/75 |
| 5,967,777 A * | 10/1999 | Klein et al. | ...................... | 433/75 |
| 6,665,574 B2 * | 12/2003 | Farren | ............................ | 700/120 |
| 6,792,327 B1 * | 9/2004 | Bamford | ....................... | 700/120 |
| 7,331,786 B2 * | 2/2008 | Poirier | ............................ | 433/75 |
| 2002/0102517 A1 * | 8/2002 | Poirier | .......................... | 433/173 |
| 2005/0084344 A1 | 4/2005 | Dods et al. | | |
| 2008/0038692 A1 * | 2/2008 | Andersson et al. | ........... | 433/167 |
| 2008/0227056 A1 * | 9/2008 | Bulard | ........................... | 433/172 |

FOREIGN PATENT DOCUMENTS

| | | | |
|---|---|---|---|
| DE | 10 2007 052 389 A1 | 5/2009 | |
| WO | WO 2007/129955 A1 | 11/2007 | |
| WO | WO 2007129955 A1 * | 11/2007 | |
| WO | WO 2008/009080 A1 | 1/2008 | |

* cited by examiner

*Primary Examiner* — Todd Manahan
*Assistant Examiner* — Matthew Nelson
(74) *Attorney, Agent, or Firm* — Scully, Scott, Murphy & Presser, P.C.

(57) ABSTRACT

The present invention concerns a drill template, comprising: a base body made by casting or rapid prototyping; at least one reinforced portion made by casting or rapid prototyping; and at least one guiding hole within the at least one reinforced portion made by drilling or milling. furthermore, the present invention concerns a method of manufacturing a drill template, comprising the steps of: forming a base body by casting or rapid prototyping; forming at least one reinforced portion by casting or rapid prototyping; and forming at least one guiding hole within the at least one reinforced portion by drilling or milling.

10 Claims, 4 Drawing Sheets

SURGICAL DRILL TEMPLATES AND METHODS OF MANUFACTURING THE SAME

BACKGROUND OF THE INVENTION

The present invention relates in general to devices for dental practices, in particular to surgical drill templates used for drilling a jaw-bone for dental implant prostheses and to methods of manufacturing these drill templates.

The drilling of a jaw-bone (mandibular or maxillary) for implanting a dental prosthesis represents a delicate surgical intervention. Precision in performing the drilling of the bone according to a selected position, depth and orientation is of extraordinary importance for a satisfactory prosthetical result.

It is a consolidated practice to carry out the drilling by means of a custom-made surgical drill template which provides for the maintenance of predetermined parameters, such as geometrical location and depth of the hole and constant angle of the drilling axis. For this purpose the drill templates are provided with guiding holes having guiding tubes. Surgical drill templates have three basic designs: tooth-supported, mucosa-supported and bone-supported templates. Additionally, these drill templates can be further divided into types with and without depth control. A custom-made drill template is usually manufactured in a series of specific work steps.

Initially, the bone situation of a jaw is analyzed by means of imaging methods, such as x-ray, magnetic resonance (MR), computer tomography (CT) or digital volume tomography (DVT). The obtained images are used to determine how much bone is available in the region designated for implantation, what implant lengths are feasible, what augmentation methods might be necessary. Furthermore, it is also used to eliminate potential injuries of important nerves (e.g. N. alveolaris inferior, N. mentalis), blood vessels, tooth roots of neighbouring teeth or paranasal sinuses. The obtained planning data are transferred to a surgical drill template which is then manufactured according to techniques that are based for example on a plaster mould (cast), the use of CAD/CAM or rapid prototyping.

Nowadays, drill templates are utilized which are manufactured by CAD/CAM methods and in which the positioning and angulation of the guiding hole is determined with great accuracy on a computer in accordance with surgical, functional and aesthetic requirements.

Although these drill templates are made with great accuracy they still have several drawbacks which are not resolved by the state of the art. In fact, the manufacturing of the drill templates carried out by means of CAD/CAM methods is complicated and entails time consuming work steps, and is therefore expensive.

On the other hand, if the drill templates are manufactured by way of rapid prototyping, costly metal guiding tubes (guiding sleeves) must be used in the guiding holes. This is due to the fact that rapid prototyping is less precise as far as the manufacturing of the guiding holes is concerned. Moreover, the drill templates made by rapid prototyping can deform during the curing and/or drying process thereof which results in a loss of accuracy of the precise structures.

The precision of drill templates produced by rapid prototyping is thus highly affected by the properties of the employed materials.

Based on the problems outlined above, one objective of the present invention is to provide a drill template which can be manufactured in a simple and cost-effective way. It is another objective of the present invention to eliminate or circumvent the deformation of drill templates, for providing drill templates with an increased precision that will allow the exact positioning and drilling of holes for tooth implants, as well as an accurate implant bed preparation and insertion.

According to the invention these objectives are achieved by providing a drill template manufactured by mixed techniques of casting or rapid prototyping combined with drilling or milling and a method of manufacturing these drill templates as cited in claim 1 and claim 8, respectively.

SUMMARY OF THE INVENTION

Accordingly, the present invention is directed to a drill template having increased precision and reduced costs.

The present invention provides a drill template comprising a base body made by casting or rapid prototyping, at least one reinforced portion made by casting or rapid prototyping and at least one guiding hole within the at least one reinforced portion made by drilling or milling.

According to the embodiments of the present invention the base body and the at least one reinforced portion are formed of materials suitable for rapid prototyping, preferably sterizable.

According to an embodiment of the present invention the drill template further comprises one or more reference points made by casting or rapid prototyping, preferably out of materials that allow easy machining or removal in subsequent operational steps. Furthermore, in the drill template according to the present invention the reference points may be provided as recesses in the drill template, and in the latter case such reference points may be used for positioning the drilling template on a milling machine and/or fixing the drilling template in stable position on the bone of the patient.

According to an embodiment of the present invention the at least one reinforced portion protrudes from the base body with a specific height and a specific surface.

According to an embodiment of the present invention the drill template may optionally comprises one or more optional guiding tubes in the at least one guiding hole.

According to an embodiment of the present invention, the optional guiding tube can be formed of materials suitable for rapid prototyping or titanium.

According to the embodiments of the present invention the drill template is a tooth-supported, mucosa-supported or bone-supported drill template or a combination thereof.

The present invention is further directed to a method of manufacturing a drill template, comprising the steps of forming a base body by casting or rapid prototyping, forming at least one reinforced portion by casting or rapid prototyping and forming at least one guiding hole within the at least one reinforced portion by drilling or milling.

The present method may also be effectively employed for modifying and putting into conformity with required surgical standards pre-existent surgical templates produced by rapid prototyping according to the state of the art, wherein holes having uneven, rough or jagged surfaces and irregularities are already incorporated during the rapid prototyping process. In fact, in these cases, it may be envisaged to refine by CAM milling such holes, previously formed by rapid prototyping.

According to a preferred embodiment of the present invention, the method further comprises the step of forming one or more reference points by casting or rapid prototyping.

According to the methods of the present invention the rapid prototyping is selected from Stereolithography (SLA), Selective Laser Sintering (SLS), Laminated Object Manufacturing (LOM), Fused Deposition Modelling (FDM), Solid Ground Curing (SGC) and Ink Jet Printing comprising Multi-Jet Modelling, Z402 Ink Jet System and Three-Dimensional Printing.

According to an embodiment of the present invention, the method further comprises optionally the step of providing the at least one guiding hole with one or more optional guiding tubes.

According to an embodiment of the present invention the method further comprises one or more steps of post-processing.

According to an embodiment of the present invention the method further comprises the step of defining a 3D image of a drill template by correlated use of imaging techniques, in cooperation with, or alternatively without the aid of, a cast of a patient.

DETAILED DESCRIPTION OF THE INVENTION

A) Surgical Drill Templates According to the Invention

Figure 1:
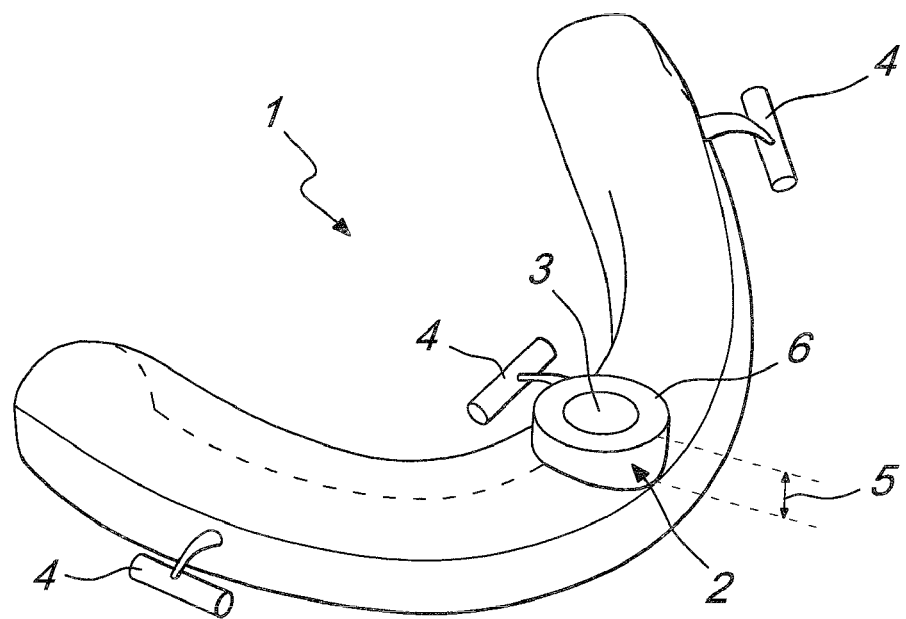
FIG. 1 shows a schematic representation of a drill template according to the invention.

Referring to FIG. 1, a schematic representation of a drill template according to the invention is shown. The drill template has a base body (1) which can be made by casting or rapid prototyping techniques or similar. The base body (1) has one reinforced portion (2). Likewise, the reinforced portion (2) can be made by casting or rapid prototyping techniques. Moreover, one guiding hole (3) is shown within the reinforced portion (2). The guiding hole (3) can be made by drilling or milling techniques.

When the guiding hole is already incorporated in a template according to the state of the art, previously manufactured by rapid prototyping, such guiding hole can be made even and precise by drilling or milling according to the present invention.

The base body (1) and the reinforced portion (2) can be made of the same material or different materials.

In a preferred embodiment of the present invention, the same material for the base body (1) and the reinforced portion (2) is used.

Depending on the technique adopted for the rapid prototyping of the base body of the templates manufactured according to the present invention, a respectively suitable material can be chosen.

For instance, liquid UV-curable photopolymer resins are used in connection with Stereolithography (SLA); whereas a wide range of commercially available powder materials, including polymers, such as nylon and polystyrene; metals, such as steel, titanium, alloy mixtures; and composites, can be used in connection with Selective Laser Sintering (SLS).

Referring to FIG. 1, the reinforced portion (2) is shown as a circular element located on the upper surface of the base body (1). However, the present invention is not limited to this design or location of the reinforced portion (2).

The reinforced portion (2) can have any design and/or location on the base body (1) which may be necessary to meet functional and surgical needs to accurately prepare an osteotomy site and place a corresponding implant.

In the embodiments according to the invention the drill templates can be further provided with or without depth control.

Referring to FIG. 1, the reinforced portion (2) is shown protruding from the base body (1) with a specific height (5) and a specific surface (6). The specific height (5) and the specific surface (6) serve as a stop position for a drill during drilling of the accurate hole for an implant (not shown). Thus, depth control can be achieved by a pre-defined height of the reinforced portion (2). The specific surface (6) is not limited to the specific surface (6) shown in FIG. 1 and can be formed to match with geometrical forms of a drill (not shown).

In an embodiment according to the invention the drill template can further comprise one or more reference points (4). The reference points (4) can be made by casting or rapid prototyping techniques or general techniques to manufacture dental templates.

It is preferred to provide the reference points (4) in specific positions, e.g. flat parts, and in specific orientations. The reference points (4) can be formed within the base body (1) and/or within the reinforced portion (2) of the drill template as cavities, e.g. rectangular, circular and the like holes, as exemplified in FIG. 4A hereinafter. Alternatively, the reference points (4) can be formed on the base body (1) and/or on the reinforced portion (2) of the drill template as protrusions, e.g. as cubes, spheres and the like, which are optionally located on rectangular, circular, and the like elongations.

Figure 3:
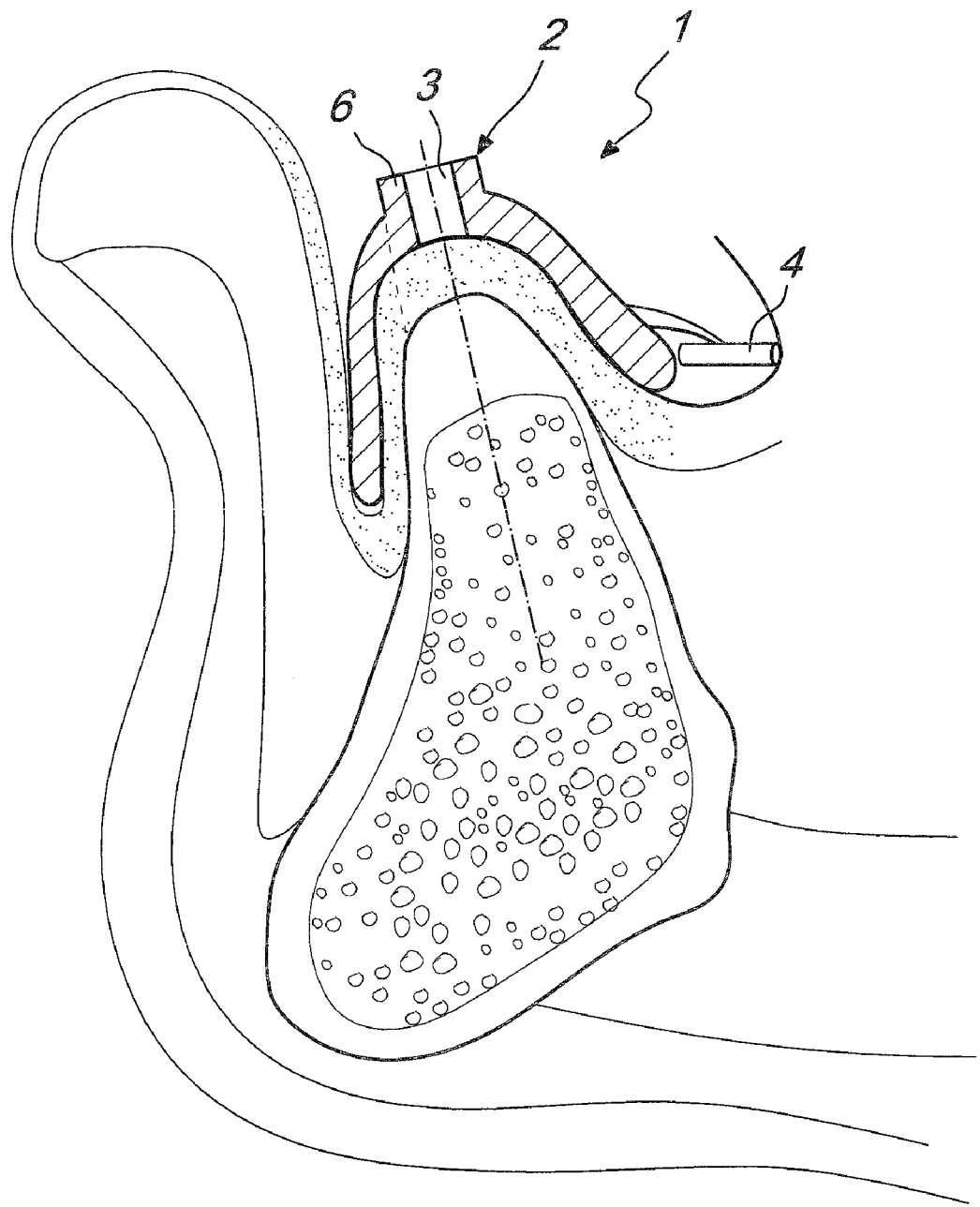
FIG. 3 shows a cross sectional representation taken line A-A of FIG. 1 with particular emphasis on the reference points which may be provided according to the present invention.

Referring to FIG. 1, the drill template is further shown with three reference points (4) formed as oblong or cubiform bodies protruding on circular elongations from the base body (1) of the drill template. A cross sectional representation of tone of the reference points (4) of FIG. 1 is shown in FIG. 3.

It is preferred in these embodiments according to the invention with protruding reference points (4) that the reference point (4) is made of the same material as the structure (base body (1) or the reinforced portion (2)) where it protrudes from. However, the materials can be also different.

The reference points (4) can be used to position the drill template in another device (e.g. a drilling or milling machine) to carry out a subsequent work step, such as adding geometries that require high precision (e.g. drilling or milling a guiding hole (3)).

In an embodiment according to the invention the protruding reference points (4) can be designed to stay on the drill template for further use in a subsequent work step, such as post-processing of the drill template.

In another embodiment according to the invention the protruding reference points (4) can be removed, e.g. by cutting them off or pulling them out, if they should disturb in a patient's mouth. In this case, the reference points (4) are made of a material that can be removed easily without leaving disturbing structures on the resulting surface. Preferred suitable materials are polymers such as plastics and similar.

In the foregoing embodiments the present invention permits to eliminate costly guiding tubes due to the shape and height of the reinforced portions (2).

Nevertheless, in an embodiment of the present invention the drill template can further comprise one or more optional guiding tubes (7) in a guiding hole (3) intended to adjust in a variable manner the diameter of the guiding hole (3).

Figure 2:
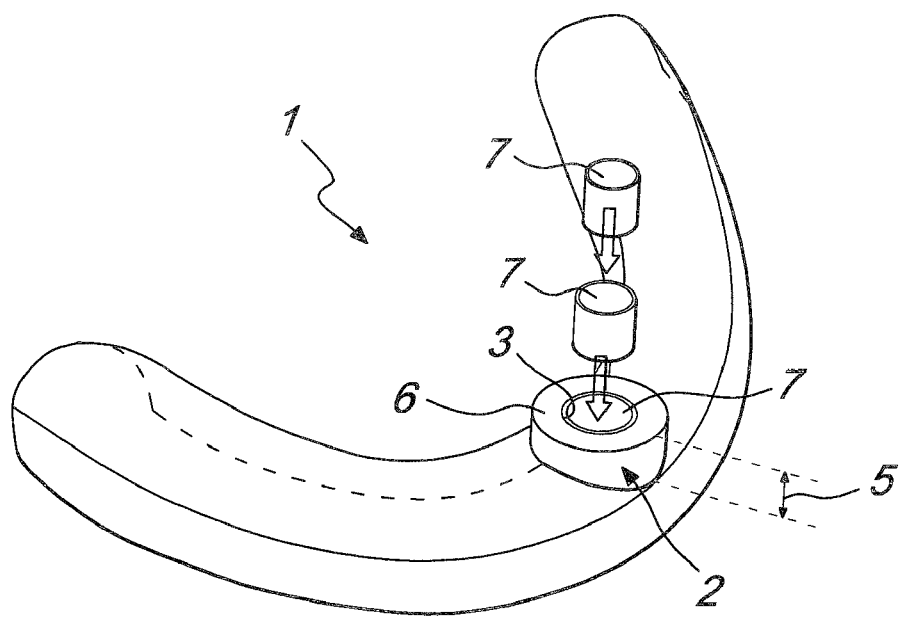
FIG. 2 shows a schematic representation of a drill template having three optional guiding tubes within one guiding hole according to the invention.

Referring to FIG. 2, a schematic representation of a drill template is shown having three optional guiding tubes (7) within the guiding hole (3). The optional guiding tubes (7) are corresponding to the diameter(s) of the utilized drill(s) (not shown) such that to match the diameter of the guiding hole (3) to the drill(s).

They can be inserted telescopically into each other and may be removed individually from the guiding hole (3). The optional guiding tubes (7) can have the specific height (5) of the reinforced portion (2), but are not limited thereto. They can serve as an additional support structure, e.g. to reduce abrasive wear during drilling and/or to contribute to the reinforced portion (2) when the wall thickness thereof is restricted to specific values.

According to an embodiment of the present invention the optional guiding tube (7) is formed of titanium alloy (TA6V), titanium grade 4, steel (INOX 316L), Cronidur®.

A substantially equivalent function as that of the above described optional guiding tubes (7) can be attained by use of a handle-retained sleeve, insertable into the hole by an operator in connection with the use of a given drill diameter.

Figure 4A:
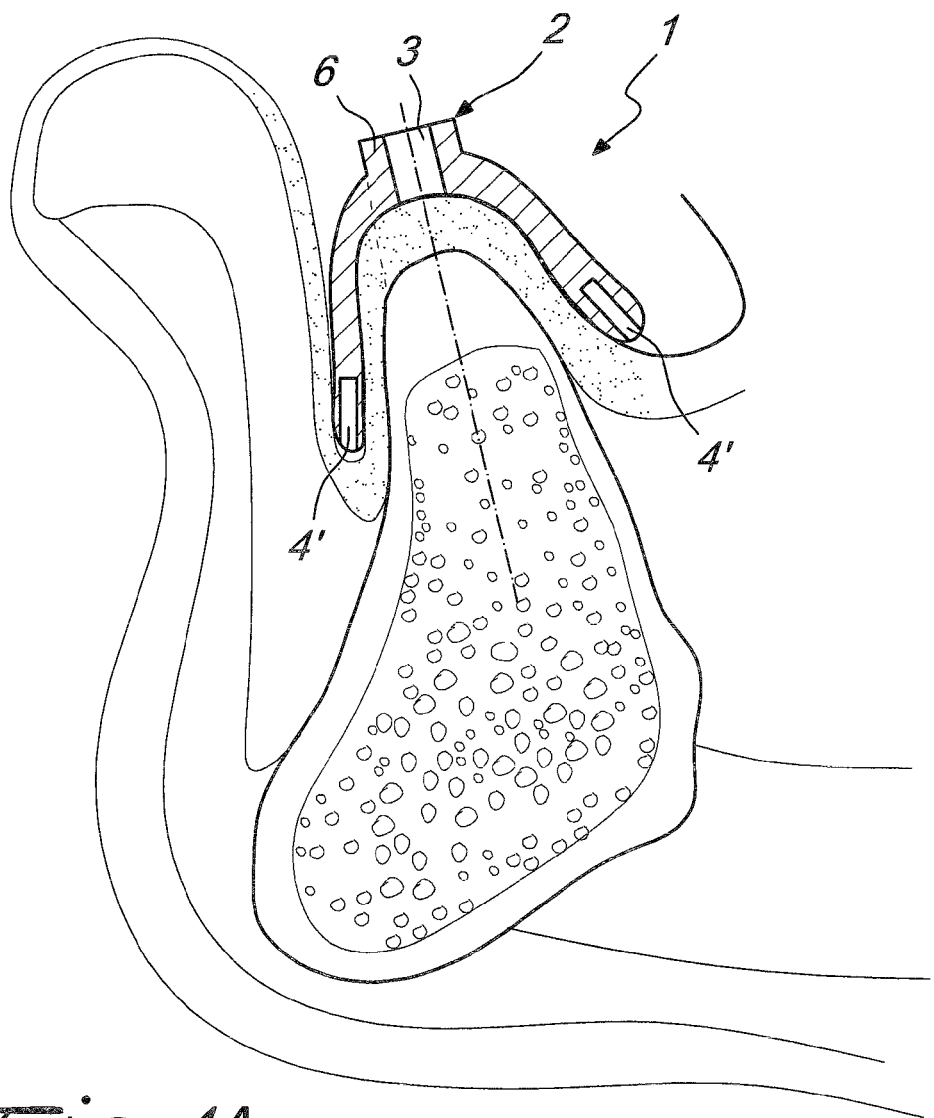
FIG. 4A shows a variation of the reference points of FIG. 3.

With reference to FIG. 4A the reference points can also be envisaged in an alternative embodiment in the form of recesses (4') in the drilling template, for instance blind holes opening at the base of the drilling template and partially running through the thickness of the template's walls.

Figure 4B:
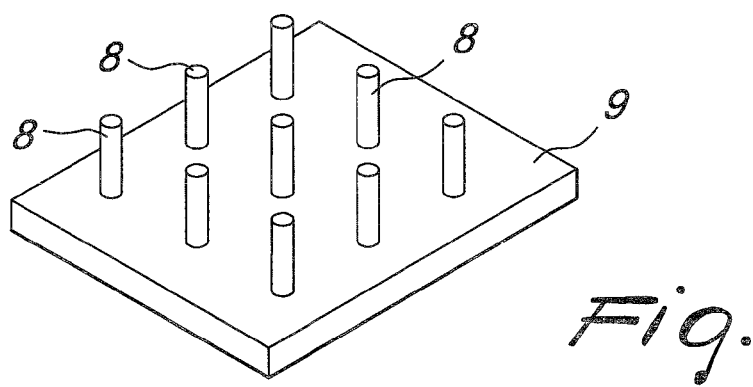
FIG. 4B shows a milling machine suitable to accommodate the drilling template having the reference points shown in FIG. 4A.

As shown in FIG. 4B such recesses (4') are apt to engage with corresponding securing pins (8) attached, at given positions, on a positioning platform (9) of a (not shown) milling machine, during milling of the guiding holes (3) in the reinforced portions (2).

In the case of reference points in form of recesses (4') as above, no parts need to be removed for fitting into a patient's mouth and similar. The reference points in form of recesses (4') may be manufactured during the process of rapid prototyping or milled in the base of the drilling template separately.

Figure 5:
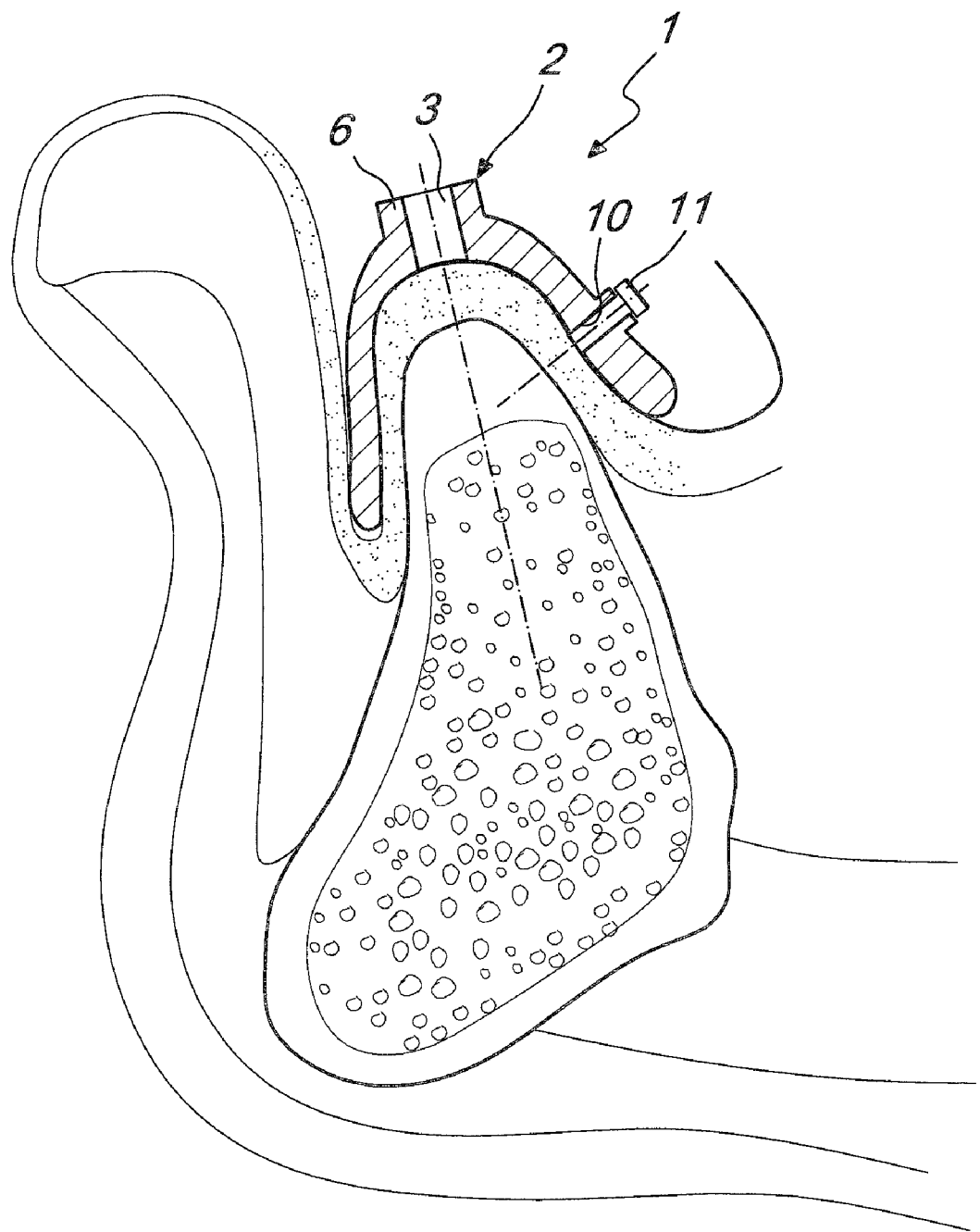
FIG. 5 shows a cross sectional representation taken along line B-B of FIG. 1 with particular emphasis on the fixation pins which may be provided according to the present invention.

With further reference to FIG. 5 the drilling template may be provided with lateral holes (10) for accommodating fixation pins (11) adapted to keep the drilling template stable on the bone during the process drilling the jaw-bone (mandibular or maxillary). The lateral holes (10) may be provided on drilling templates with or without reference points. The lateral holes (10) may be manufactured during the process of rapid prototyping or milled in the base of the drilling template separately.

B) Methods of Manufacturing the Surgical Drill Templates According to the Invention The present invention is further directed to a method of manufacturing a drill template. The method comprises the step of forming a base body (1) by casting or rapid prototyping techniques. In the next step, a reinforced portion (2) is formed by casting or rapid prototyping techniques.

The forming of the reinforced portion (2) can also be executed concurrently with the forming of the base body (1).

Subsequently, a guiding hole (3) is formed within the reinforced portion (2) by drilling or milling techniques.

The method of manufacturing a drill template can further comprise the step of forming one or more reference points (4) by casting or rapid prototyping techniques.

For manufacturing the drill templates the same materials are used that are described in combination with individual elements of the invention in section A) above.

According to the methods of the present invention the rapid prototyping is selected from Stereolithography (SLA), Selective Laser Sintering (SLS), Laminated Object Manufacturing (LOM), Fused Deposition Modelling (FDM), Solid Ground Curing (SGC) and Ink Jet Printing comprising Multi-Jet Modelling, Z402 Ink Jet System and Three-Dimensional Printing.

As mentioned above, a guiding hole (3) is formed within the reinforced portion (2) by drilling or milling techniques. It is preferred to carry out the drilling or milling by CAD/CAM drilling and milling, respectively. For example, CNC machines having 3, 4 or 5 axes can be used to transfer the guiding hole (3) into a physical model of the drill template.

According to a method of the present invention the method can further comprise one or more steps of post-processing, such as sterilization or addition of further geometries or of tubes for several purposes.

For instance, some holes in the template can be partially opened, so as to allow lateral insertion of instruments into the template.

Entities apt to fix the template to a previously placed implant or screw can be also milled, as well as geometries apt to fix a transfer piece.

Reference numbers as well as possible text can be milled, etched or similar in correspondence with the holes, in order to provide the surgeon with useful information on correctly following the surgical procedure.

According to a method of the present invention the method can further comprise the step of defining a 3D image of a drill template by correlated use of imaging methods and a plaster mould or cast of a patient. Examples of imaging methods are x-ray, magnetic resonance (MR), computer tomography (CT) or digital volume tomography (DVT). Digital volume tomography (DVT) is preferred to its clearly reduced radiation load compared to computer tomography (CT).

According to another aspect of the present invention a try-in prosthesis can be manufactured by rapid prototyping (e.g. stereolithography) and reference points (4) having the above mentioned features can be provided. The reference points (4) can help in a later work step to adapt the try-in prosthesis and to build a surgical drill template out of it in a milling machine (e.g. 5-axis milling machine).

The advantages achieved by the present invention can be substantially described as follows:

The drill templates designed according to the present invention have an increased precision and can be produced with tighter tolerances.

When a multiplicity of holes is practiced in the template, the position of the respective axes can be optimally controlled thanks to the method according to the present invention.

A possible deformation of the rapid prototyping drill template, e.g. during drying and/or curing, represents no problem at all, since structures needing to have high accuracy, such as the guiding hole (3), are fabricated in a later step by means of automated machines apt to execute operations in a totally controlled way, based on a computer file.

For milling a complex form of the drill template directly with a milling machine, the complex forms (e.g. a narrow radius or complex teeth geometry) would have to be adjusted for the CAM in order to comply with the manufacturing precision of the milling machine Thanks to the present invention this work step is not required anymore, since these overall complex structures can be made by rapid prototyping techniques according to the invention.

Moreover, the drill templates according to the invention can eliminate the necessity of costly metal sleeves within the guiding holes (3) due to the provision of machine milled guiding holes in the reinforced portions (2). Narrower holes can thus be incorporated in the surgical templates, which is in the first place desirable for the purposes of their structural resistance and stability.

As a result, the drill templates according to the invention can be manufactured in a simple way with decreased delivery times and reduced costs.

The disclosures in European Patent Application no. 09157189.3, from which this application claims priority, are incorporated herein by reference.

What is claimed is:

1. A method of manufacturing a drill template for drilling a jaw bone for dental implant prostheses, comprising the steps of:
    forming a base body by casting or rapid prototyping;
    forming at least one reinforced portion by casting or rapid prototyping; and
    forming at least one guiding hole within the at least one reinforced portion by drilling or milling.

2. The method of claim 1, further comprising the step of forming one or more reference points by casting or rapid prototyping.

3. The method of claim 1, wherein the at least one reinforced portion is formed to protrude from the base body with a specific height and a specific surface.

4. The method of claim 1, further comprising the step of providing the at least one guiding hole with one or more guiding tubes.

5. The method of claim 1, further comprising one or more steps of post-processing.

6. The method of claim 1, wherein the rapid prototyping is selected from the group comprising Stereolithography (SLA), Selective Laser Sintering (SLS), Laminated Object Manufacturing (LOM), Fused Deposition Modelling (FDM), Solid Ground Curing (SGC) and Ink Jet Printing comprising Multi-Jet Modelling, Z402Ink Jet System and Three-Dimensional Printing.

7. The method of claim 1, further comprising the step of forming reference points on the base body and/or on the reinforced portion of the drill template as protrusions by means of rapid prototyping or milling.

8. The method of claim 1, further comprising the step of forming reference points within the base body and/or within the reinforced portion of the drill template as cavities by means of rapid prototyping or milling.

9. The method claim 1, further comprising the step of forming lateral holes for accommodating fixation pins adapted to keep the drilling template stable on the bone during the process drilling the mandibular or maxillary jaw-bone, the lateral hole being provided in the base body of the drilling template, the lateral holes being formed by means of rapid prototyping or milling.

10. The method of claim 1, further comprising the step of defining a 3D image of a drill template by correlated use of imaging methods and a cast of a patient.

* * * * *